(12) United States Patent
Arkles et al.

(10) Patent No.: US 6,881,849 B2
(45) Date of Patent: Apr. 19, 2005

(54) SULFOLANE FUNCTIONAL SILANES, COMPOSITIONS, AND METHODS OF USE OF THE SAME

(75) Inventors: Barry C. Arkles, Dresher, PA (US); Youlin Pan, Langhorne, PA (US)

(73) Assignee: Gelest, Inc., Morrisville, PA (US)

( * ) Notice: Subject to any disclaimer, the term of this patent is extended or adjusted under 35 U.S.C. 154(b) by 0 days.

(21) Appl. No.: 10/193,882

(22) Filed: Jul. 12, 2002

(65) Prior Publication Data

US 2003/0060636 A1 Mar. 27, 2003

Related U.S. Application Data

(60) Provisional application No. 60/304,910, filed on Jul. 12, 2001.

(51) Int. Cl.[7] ............................. C07F 7/02; B01D 12/00
(52) U.S. Cl. .......................................... 549/4; 516/200
(58) Field of Search ............................. 549/4; 516/200

(56) References Cited

U.S. PATENT DOCUMENTS 4,049,674 A  *  9/1977 Kanner et al.
4,049,675 A  *  9/1977 Kanner et al. ................. 549/4
4,049,676 A  *  9/1977 Schilling, Jr.

OTHER PUBLICATIONS

Narkevitch et al, J. Org. Chem., vol. 66, pp 5080–5093, 2001.(Published on Web on Jul. 4, 2001).*

Arkles, B., et al., "Factors contributing to the stability of akloxysilanes in aqueous solution," *Silanes and Other Coupling Agents,* pp. 91–104 (1992) Ed. K.L. Mittal.

Purdy, A., et al., "Synthesis of High–Dielectric, Crosslinked Silicone Materials," *Polymeric Materials: Sicence & Engineering 2001,* 84, pp. 641–642.

* cited by examiner

*Primary Examiner*—Shailendra Kumar
(74) *Attorney, Agent, or Firm*—Akin Gump Strauss Hauer & Feld, LLP

(57) ABSTRACT

The invention includes a sulfolane functional silane comprising a sulfolane ring, an alkoxy group, a hydrocarbon backbone, and a silyl moiety. An oxygen atom of the alkoxy group is bound to the sulfolane ring, and the hydrocarbon backbone has one to fifty carbon atoms and is bound by its first terminal carbon atom to a carbon of the alkoxy group and by its second terminal carbon atom to the silicone atom of the silyl moiety. The silyl moiety comprises at least one hydrolyzable group and/or a non-hydrolyzable group that is a substituted or unsubstituted siloxane group. A method to stabilize a silane solution is described and includes adding the sulfolane functional silane of the invention to a solution containing silane hydrosylates.

39 Claims, No Drawings

SULFOLANE FUNCTIONAL SILANES, COMPOSITIONS, AND METHODS OF USE OF THE SAME

CROSS-REFERENCE TO RELATED APPLICATIONS

This patent application claims the benefit of priority of provisional U.S. Patent Application No. 60/304,910, filed Jul. 12, 2001, the disclosure of which is incorporated herein by reference.

BACKGROUND OF THE INVENTION

Organofunctional silanes are known in the art as coupling agents, adhesion promoters, and surface modifiers. For example, silicate esters, typically alkoxysilanes, such as methacryloxypropyltrimethoxysilane, octyltriethoxysilane, and/or tetraethoxysilane, are used in the preparation of ceramic coatings and binders to improve adhesion, and for surface modification. In most commercial silane surface treatment applications, the alkoxy groups of alkoxysilanes are hydrolyzed to form silanol-containing species, which are highly reactive intermediates responsible for bond formation with a substrate. Hydrolysis of the alkoxy groups may occur during the formal preparation of aqueous silane solutions or by the reaction of the silane with adsorbed moisture on substrate surfaces. A general overview of the reaction and bonding mechanism of alkoxysilanes may be found, for example, in Arkles, B. et al., *Factors Contributing to the Stability of Alkoxysilanes in Aqueous Solution*, Silanes and Other Coupling Agents, pp. 91–104, ed. K. Mittal (1992).

In aqueous environments, most silanols used in surface treatment applications are unstable in their monomeric form. Once hydrolysis is initiated, these silanols may condense relatively quickly within hours with other silanols and their alkoxy precursors, forming gels or precipitates which have no utility for surface modification. Trialkoxysilanes are known to be more stable sources for silanols, but have numerous disadvantages, including production of hydrolysis by-products that are undesirably toxic and/or flammable, and difficult to remove from solution.

Several methods have been employed in the prior art to stabilize silane solutions. For example, one approach has been to cohydrolyze a hydrophilic silane with a surface modifying silane, forming silanol-rich oligomeric condensates. These silanes maintain greater silanol stability in solution and exhibit substantially greater wet bond strength relative to conventional silanes.

Thus, there is a great need in the art for an organofunctional silane that is useful on surface application modifications, would facilitate the hydrolysis of the other silanes in solution and be more effective in stabilizing the reactive species while in solution.

BRIEF SUMMARY OF THE INVENTION

The invention includes a sulfolane functional silane comprising a sulfolane ring, an alkoxy group, a hydrocarbon backbone, and a silyl moiety. An oxygen atom of the alkoxy group is bound to the sulfolane ring, and the hydrocarbon backbone has one to fifty carbon atoms and is bound by its first terminal carbon atom to a carbon of the alkoxy group and by its second terminal carbon atom to the silicone atom of the silyl moiety. The silyl moiety may comprise at least one non-hydrolyzable group(s) and/or at least one hydrolyzable group.

The invention also provides a sulfolane functional silane represented by the formula (VII):

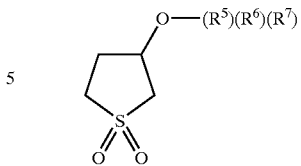

The group represented by "$R^5$" is selected from (i) a substituted or unsubstituted alkyl group having one to ten carbon atoms and (ii) the group ($—R—O)_n$, where R is a substituted or unsubstituted, linear or branched alkyl group having one to seven carbon atoms, and n is an integer of 1 to 12. $R^6$ is a substituted or unsubstituted alkyl group having one to fifty carbon atoms and $R^7$ is a silyl moiety that comprises a group selected from a hydrolyzable group and a siloxane group.

A method to stabilize a silane solution is encompassed within the invention. The method includes adding the sulfolane functional silane of the invention to a solution containing silane hydrosylates.

Another aspect of the invention is an elastomeric composition comprising an elastomeric polymer and a sulfolane functional silane of the invention, as well as a method of enhancing the wettability of an elastomeric composition. This method includes compounding an uncured elastomeric polymer with an additive, wherein the additive comprises the sulfolane functional silane of the invention.

DETAILED DESCRIPTION OF THE INVENTION

The invention described herein is a specific class of sulfolane functional silanes which are useful in preparing hydrophilic surfaces, in wetting and surfactant applications, and which serve to facilitate the hydrolysis of other silanes and to stabilize solutions containing silane hydrosylates. The invention also includes a surfactant/wetting composition containing the sulfolane functional silanes of the invention, methods of preparing the sulfolane functional silanes of the invention, and methods of stabilizing silane solution using the compound of the invention.

The sulfolane functional silane of the invention may be used as a coupling agent, adhesion promoter, and surface modifier, among other applications.

The invention described is a sulfolane functional silane, having a sulfolane ring and a silyl moiety. The silyl moiety can include at least one hydrolyzable group that can participate in adhesion and surface modification reactions and/or at least one non-hydrolyzable group, such as a siloxane group. Also described is a method of preparing the sulfolane functional silane, a method for stabilizing aqueous silane solutions, and wetting and/or surfactant compositions including the sulfolane functional silanes of the invention. Compositions or silanol containing solutions made with the sulfolane functional silane of the invention are sufficiently stable such that the silanol intermediates may not undergo condensation to form gels or precipitates, thereby improving the efficiency of the process of bond formation with the substrate, when the solution is used in such application.

The sulfolane functional silanes of the invention are hydrophilic. Simple structural modifications, as is known or to be developed in the art, can be performed to achieve differing degrees of hydrophilicity, depending on the use/application for which the final product is intended. Modifications to alter the degree of hydrophilicity can include, for example, the inclusion/omission of hydrophilic groups as substitutions to any of the component moieties of the sulfolane functional silanes, and/or including hydrophilic groups along the primary carbon chain of the sulfolane functional silanes of the invention.

As used in the context of this specification, "branched" refers to any molecule other than a straight chain molecule. "Aliphatic" refers to an organic compound that does not contain an aromatic ring. "Aromatic" is used herein to describe a benzene or a benzene-derived ring having a resonance structure.

"Hydrophilic" refers to a compound that has a strong tendency to bond or absorb water, a tendency to dissolve in water, and/or is readily mixed with or wetted by water.

"Hydrolyzable" describes a compound or group capable of being hydrolyzed in the presence of water or an —OH species. In contrast "non-hydrolyzable," as used herein refers to compounds or groups which do not substantially undergo hydrolysis in the presence of water or an —OH containing species.

As used herein, "substituted" means an organic or hydrocarbon structure in which one or more of the bonds or atoms is replaced by a substituent group, such as a linear or branched functional group, alkyl groups, ionic groups, and the like.

The description provided herein details several embodiments of the invention; however, it should be understood that the invention is not limited to the embodiments described.

The invention provides a sulfolane functional silane including (i) a sulfolane ring, (ii) an alkoxy group bound to the sulfolane ring, (iii) a hydrocarbon backbone bound to a carbon of the alkoxy group, and (iv) silyl moiety. The sulfolane functional silane of the invention contains a sulfolane ring that includes 1,1-dioxide tetrahydrothiofuran (tetra-methylene sulfone). The sulfolane ring may be represented by the formula (I):

(I)

The sulfolane ring may be unsubstituted or substituted by any groups known or to be developed in the art, as long as the substitutions do not substantially alter the sulfolane functionality of the sulfolane functional silane of the invention. If substituted, the substituted groups may be, for example, independently selected from $C_1$ to $C_5$ alkyl or alkoxy groups, with methyl groups being the more preferred substituents.

The sulfolane functional silanes of the invention further include an alkoxy group. An oxygen atom of the alkoxy group is bound to a carbon atom of the sulfolane ring. The oxygen atom of the alkoxy group may be bound to any of the four carbons present in the sulfolane ring; however, it is preferred that the oxygen atom of the alkoxy group is bound at the C-1 position or at the C-2 position of the sulfolane ring.

The alkoxy group may be branched or linear, substituted or unsubstituted, although linear and/or unsubstituted is preferred. If substituted, groups which may be substituted into the alkoxy chains include all known or to be developed in the art, such as alkyl groups, allyl groups, alkoxy groups, halogens, vinyl groups, hydroxyl groups, phenyl groups, phenoxyl groups, cyano groups and/or amino groups.

The alkoxy group of the sulfolane functional silane may be any alkoxy group known in the art. It is preferred that it is a $C_1$ to $C_7$ alkoxy group, and most preferred that it is a $C_1$ to $C_4$ alkoxy group. Alternatively, the alkoxy group of the sulfolane functional silane of the invention may be represented by the formula:

wherein R is a linear or branched, substituted or unsubstituted alkyl group, and "n" is an integer of 1 to 12, preferably an integer of 1 to 5, and most preferably, n is the integer 4. The group represented by R may preferably be a substituted or unsubstituted linear or branched $C_1$ to $C_7$ alkyl group; it is more preferred that R is a $C_1$ to $C_4$ alkyl group.

As will be recognized by a person of skill in the art based upon this disclosure, one means by which the hydrophilicity of the sulfolane functional silane of the present invention can be increased or decreased is by altering the value of "n" in formula (II). For example, if the sulfolane functional silane of the invention is to be used in certain bonding/adhesion applications, it may be preferable that the group represented by formula (II) is —O—$CH_2$—$CH_2$—O)$_3$, —O—($CH_2$—$CH_2$—O)$_4$, or —O—($CH_2$—$CH_2$—O)$_5$, depending on the degree of hydrophilicity desired.

The sulfolane functional silane of the invention also includes hydrocarbon backbone of one to fifty carbon atoms. The number of carbon atoms present in the hydrocarbon backbone may be varied by one of ordinary skill depending several considerations, including for example, the identity and/or chemical nature of the remaining component moieties of the sulfolane functional silane of the invention, and/or the chemical/physical property or properties desired in the end product. However, it is preferred that the hydrocarbon backbone contains one to ten carbon atoms, and most preferably contains one to three carbon atoms.

The hydrocarbon backbone of the sulfolane functional silane described herein has two terminal carbon atoms, a first terminal carbon atom and a second terminal carbon atom. While there may be other groups having "terminal" carbon atoms in the sulfolane functional silane if it is branched or substituted, it is the two terminal carbon atom groups of the hydrocarbon backbone referred to herein. To the first terminal carbon atom of the hydrocarbon backbone is bound a carbon atom of the alkoxy group discussed supra.

The second terminal carbon atom of the hydrocarbon backbone is bound to the silicon atom of the silyl moiety, which is described in greater detail below. The backbone is preferably aliphatic (linear) although aromatic group(s) may be included along the hydrocarbon backbone chain. The hydrocarbon backbone may be substituted or unsubstituted; substitutions may be made along the backbone chain, as long as the relative locations of the sulfolane ring and the silyl moiety are substantially maintained as described herein.

Groups with which the hydrocarbon backbone may be substituted include all known or to be developed in the art, for example, a halogen, an alkyl group, an allyl group, a vinyl group, a hydroxyl group, a phenyl group, a phenoxyl group, a trialkylsiloxy group, a cyano group, and/or an amino group.

The sulfolane functional silanes of the invention also include a silyl moiety. The silyl moiety of the invention is a silyl group represented by the formula $H_3Si$— but wherein at least one hydrogen atom, preferably two to three of the hydrogen atoms, substituted with a hydrolyzable and/or non-hydrolyzable group as described herein.

As will be understood by a person of skill in the art based upon this disclosure, the number, type, and specific permutation of hydrolyzable and/or non-hydrolyzable groups of the silyl moiety may be varied, depending on the chemical property or properties desired in the finished sulfolane functional silane product and/or the application in which the sulfolane functional silane is intended to be used.

As explained above, the second terminal carbon atom of the hydrocarbon backbone is bound to the silicon atom of this silyl moiety. In one embodiment of the invention, the silyl moiety of the sulfolane functional silane of the invention includes at least one hydrolyzable group. Preferably the silyl moiety contains two or three hydrolyzable groups.

If greater than one hydrolyzable group is present in the silyl moiety, the groups may be the same, or they may be different. The selected hydrolyzable groups should be capable of reacting with a selected substrate and may therefore be varied or functionalized for use with a selected substrate or for use in facilitating hydrolysis and/or stabilizing solutions of silanes. Preferred substrates include, for example, silicon dioxide, and other metal oxides.

Hydrolyzable groups for use in the sulfolane functional silane of the invention include, without limitation, carboxylates, such as acetoxy and propenenoxy, halogens, such as, for example, chlorine, fluorine, bromine, and iodine; alkylamines and dialkylamines, such as, for example, methylamaine, ethylamine, propylamine, isopropylamine, butylamine, isobutylamine, pentylamine, hexylamine, dimethylamine, diethylamine, methylethylamine, dipropylamine, methylpropylamine, ethylpropylamine, and similar compounds; and alkoxy groups, such as, for example, methoxy, ethoxy, propoxy, isopropoxy, butoxy, and groups represented by the formula (III):

$$—O—R^2 \qquad (III)$$

The group represented by $R^2$ of formula (III) may be an alkyl group, an alkylamine group, a dialkylamine group, a cyanoalkyl group, an allyl group, a vinyl group, an acetyl group, or a cyano group.

Preferably, the hydrolyzable group(s) of the silyl moiety is a chlorine atom, and/or an alkoxy group, such as methoxy or ethyoxy. However, other hydrolyzable groups having similar properties may be used, or other groups may be selected for reactions with non-silicon-containing substrates, as is known or to be developed in the art.

If the terminal silyl moiety includes one or two hydrolyzable group(s), the moiety can additionally contain any other non-hydrolyzable group, as is known or to be developed in the art. For example, it may contain at least one linear or branched, substituted or unsubstituted alkyl chain of one to four carbon atoms, an aryl group, and/or a hydrogen atom. Additional options for non-hydrolyzable groups are discussed in more detail, infra.

In an embodiment of the invention, the silyl moiety is represented by the formula:

$$—Si(R^3)_m(R^4)_{3-m} \qquad (IV)$$

wherein $R^3$ is independently a substituted or unsubstituted alkyl group having one to three carbon atoms or hydrogen atom, and $R^4$ is independently selected from a halogen (such as a chlorine atom or a fluorine atom), and/or a alkoxy group having one to three carbon atoms. The "m" of formula (IV) is an integer of 0 to 2.

Depending on the application in which the sulfolane functional silane is intended to be used, the silyl moiety can include at least one non-hydrolyzable group, including all non-hydrolyzable groups known or to be developed in the art. If more than one non-hydrolyzable group is present in the silyl moiety, they can be the same or they can be different from one another. Exemplary non-hydrolyzable groups include a hydrogen atom, substituted or unsubstituted alkyl groups or aryl groups, and substituted or unsubstituted siloxane (oxosilane) groups represented by the formula (V):

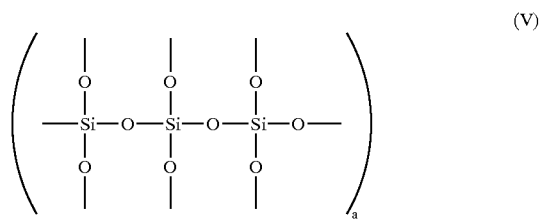

In formula (V), "a" is an integer of 1 to 12. Preferred siloxane groups include substituted and unsubstituted disiloxane group and trisiloxane groups.

If the sulfolane functional silane of the invention is intended to be used in a surfactant application, it may be preferable that the silyl moiety includes at least one non-hydrolyzable group that is a substituted or unsubstituted siloxane group. For example, it may be preferred that the silyl moiety comprise at least one, or two to three, substituted siloxane groups. Suitable groups for substitution of the siloxane groups include $C_1$ to $C_8$ alkyl groups. More preferred are siloxane groups substituted with methyl group(s), ethyl group(s), and propyl group(s).

In an embodiment of the invention, the silyl moiety is represented by the formula:

$$—Si(R^8)_p(R^9)_{3-p} \qquad (VI)$$

wherein $R^8$ is independently a substituted or unsubstituted alkyl group having one to three carbon atoms or a hydrogen atom, and $R^9$ is independently selected from a substituted or unsubstituted siloxane group. The "p" of formula (VI) is an integer of 0 to 2.

The sulfolane functional silane, as described, above, preferably has the following formula (VII):

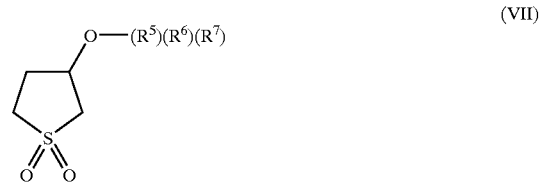

wherein $R^5$ is selected from: (i) a substituted or unsubstituted, branched or linear alkyl group having one to ten carbon atoms and (ii) the group $(—R—O)_n$, wherein R is a substituted or unsubstituted, linear or branched alkyl group having one to seven carbon atoms, and "n" is an integer of one to twelve. The group represented by $R^6$ is a substituted or unsubstituted alkyl having one to fifty carbon atoms, but preferably one to ten carbon atoms, and most preferably, three carbon atoms. The group represented by $R^7$ is independently at least one hydrolyzable group. Hydrolyzable groups suitable for $R^7$ include all those listed above.

The group represented by $R^7$ may be represented by the formula (IV):

$$—Si(R^3)_m(R^4)_{3-m} \qquad (IV)$$

wherein $R^3$ is independently an alkyl group having one to three carbon atoms, and $R^4$ is independently selected from a halogen, a chlorine atom, and an alkoxy group having one to three carbon atoms, and "m" is an integer of 0 to 2.

In a further embodiment, the group represented by $R^7$ may be the silyl moiety represented by the formula (VI):

$$—Si(R^8)_p(R^9)_{3-p} \qquad \text{(VI)}$$

wherein $R^8$ is independently a substituted or unsubstituted alkyl group having one to three carbon atoms or a hydrogen atom, and $R^9$ is independently selected from a substituted or unsubstituted siloxane group. The "p" of formula (VI) is an integer of 0 to 2.

The sulfolane functional silanes of the invention may be prepared by any chemical pathway/reaction series known or to be developed in the art. In general, the organofunctional silanes of the invention may be obtained by first preparing or obtaining an allyloxysulfolane. This can be accomplished by any techniques or methods known or to be developed in the art.

For example, allyloxysulfolane may be prepared by reacting a sulfolane with an allyl alcohol, preferably in excess, such as, for example, two to six times in excess, in the presence of an —OH species, such as, for example, potassium hydroxide, sodium hydroxide, ammonium hydroxide, and/or lithium hydroxide.

Alternatively, a commercially available allyloxysulfolane may be used in preparation of the organofunctional silane of the invention.

Once obtained, the allylalkoxysulfolane is reacted with a monomeric silane, in the presence of a metal-containing catalyst. Preferred monomeric silanes include trichlorosilane, trihalosilane, trialkoxy silanes, and trialkylsiloxysilanes.

Metal-containing catalysts that may be used to facilitate the reaction include platinum complex catalysts ("Pt—" catalysts) such as, for example, platinum-divinyltetramethyldisiloxane complex, platinum-cyclovinyl methylsiloxane complex, platinum-tetramethyldisiloxane complex, chloroplatinic acid, chloroplatinic acid complexes and/or solutions, and tris-triphenyl phosphine rhodium chloride. More preferable, the metallic catalyst is a platinum-divinyltetramethyldisiloxane complex.

The reaction may be carried out with an excess (preferably about a 10% excess) of the monomeric silanes; however this is not necessary. All, or optionally only a portion, of the monomeric silane is initially added to alkoxysulfolane, which is preferably in a liquid medium, or more preferably, in a solvent medium. The metallic catalyst may be charged to the reaction mixture. The reaction mixture should then be heated to a temperature of from about 30° C. to 200° C., preferably from about 60° C. to about 160° C. It is preferred that the heating takes place under substantially oxygen-free conditions. An exotherm, typically moderate, may occur, at which time, the remaining amount of alkylsilane monomer, if not already added, may be added to the reaction mixture, while maintaining the temperature in the range set out above.

Each reaction may be followed by a distillation step, as is known in the art, to obtain a purified product, or such product may be obtained by any means known or to be developed in the art.

The sulfolane functional silane of the invention is useful in numerous applications including, for example, as a coupling agent, an adhesion promoter and/or a surface modifier. The sulfolane functional silane of the invention may be compounded with a rubber or an elastomer in order to enhance wettability of the finished composition. It is preferred that the sulfolane functional silane of the invention is compound with an uncured elastomeric polymer, and cured to form an elastomeric composition. The uncured elastomeric polymer may be any known or to be developed in the art, including, for example, styrene-butadiene copolymers, polychloroprene (neoprene), nitrile rubber, butyl rubber, polysulfide rubber, cis 1,4-polyisoprene, ethylene-propylene terpolymers (EDPM rubber), silicone rubber, and polyurethane rubber. Most preferably, the uncured elastomeric polymer is a silicone rubber. The uncured elastomeric polymer may be compounded with the sulfolane functional silanes of the invention as an additive or a processing aid. In particular, the invention is a method of enhancing the wettability of a cured elastomeric composition by compounding one or more sulfolane function silanes of the invention with an uncured elastomeric polymer, and curing, thereby enhancing the wettability of the resultant elastomeric composition.

The sulfolane functional silane of the invention can be used to stabilize or improve the stability of a solution containing silanes, and/or to facilitate the hydrolysis of other silanes in the solution by adding the sulfolane functional silane of the invention to a solution containing silanes.

The sulfolane function silanes of the invention may also be used as a surfactant or wetting agent.

The invention is further described by the following non-limiting examples.

EXAMPLE 1

An allyloxysulfolane for use in the preparation of the sulfolane functional silane of the invention was prepared. A 1 liter single neck round bottom flask equipped with a magnetic stirrer, condenser and water bath was charged with 232.3 g of allyl alcohol (two-fold excess), 235.3 g of sulfolene (butadiene sulfone), and 11.5 g of potassium hydroxide, and stirred at approximately 30° C. for approximately 24 hours.

The condenser was removed and the mixture acidified to a pH of 2 by addition of approximately 20 mls of concentrated HCl. The water bath was removed and replaced with a heating mantle. A distillation head was mounted on the flask. The mixture was distilled at atmospheric pressure to a pot temperature of 120° C. followed by vacuum at about 20 mm to remove excess allyl alcohol. Vacuum was increased to 0.6 mm. Approximately 343 g (96.6% yield) of allyloxysulfolane was recovered. The allyloxysulfolane obtained exhibited the following properties: purity 99.3% by gas chromatography; boiling point was 135° C. at 0.6 mm, the density of the compound was 1.198 at 23° C., and the refractive index of the compound was 1.4920 at 23° C.

EXAMPLE 2

A sulfolane functional silane of the invention was prepared. The specific sulfolane functional silane prepared was trichlorosilylpropoxysulfolane. A 1-liter three-neck round bottom flask that was under a positive pressure of nitrogen was equipped with a magnetic stirrer, dry-ice condenser, addition funnel, and pot thermometer and was charged with 132.2 g of the allyloxysulfolane of Example 1 and 10 ml of tetrahydrofuran. The mixture was warmed to approximately 85° C. and 101.6 g of trichlorosilane was added followed by 1 ml of a metallic catalyst, platinum-divinyltetramethyldisiloxane solution in xylene (2 wt % Pt). A moderate exotherm was observed and the balance of the trichlorosilane was added at a rate to maintain the temperature between 80°–140° C. The mixture was then stirred for 24 hours at 90° C. The mixture was distilled. The purified trichlorosilylpropoxysulfolane thereby obtained had a boiling point in the range of 170°–172° C. at 0.5 mm and a density of 1.385 at 27° C. Overall yield of product was 71.5% at 97% purity.

EXAMPLE 3

A sulfolane functional silane of the invention was prepared. The specific sulfolane functional silane prepared was triethoxysilylpropoxysulfolane. A 1 liter three-neck round bottom flask that was under a positive pressure of nitrogen was equipped with a magnetic stirrer, condenser, addition funnel, and pot thermometer and was charged with the trichlorosilylpropoxysulfolane from Example 2. The flask and its contents were then heated to 90° C. Triethylorthoacetate (365.0 g) was added while maintaining the temperature between 90°–150° C. By-products ethyl chloride and ethyl acetate were allowed to vent. Completion of the reaction was checked by gas chromatography and by adding a small aliquot of the reaction mixture to water and checking for neutral pH. The product was distilled. The purified triethocysilylpropoxysulfolane thereby obtained had a boiling point of 187°–190° C. at 0.5 mm and a density of 1.125 at 24° C. Overall yield was 71.5% at 97% purity.

EXAMPLE 4

Under conditions similar to those of Example 2, a 500 ml three-neck round bottom flask equipped with a magnetic stirrer, dry-ice condenser, addition funnel, and pot thermometer and under a positive pressure of nitrogen was charged with 132.2 g of allyloxysulfolane and 50 g of bis(trimethylsiloxy)methylsilane. Initially, the mixture was two phases. The mixture was heated to approximately 70° C., then 1 ml of platinum-divinyltetramethyldisiloxane solution in xylene (2 wt % Pt) was added. A very mild exotherm was observed and the mixture was heated to 110° C. The mixture was then stirred for 16 hours. The mixture was distilled. The purified bis(trimethylsiloxy)methylsilylpropoxysulfolane had a boiling point of approximately 152°–154° C. at 0.4 mm, a density of 1.034 at 22° C., and a refractive index of 1.445 at 25° C.

EXAMPLE 5

A 500 ml three neck round bottom flask equipped with magnetic stirrer, condenser, addition funnel, and pot thermometer was charged with 165.0 g (0.75 mol) of allyloxyethyloxy sulfolane under a positive pressure of nitrogen. After heating to 80–90° C., 45.2 g (0.28 mol) of triethyoxysilane was added, followed by 1 ml of Pt(0)-divinyltetramethyldisiloxane solution in xylene (2 wt % Pt). The pot temperature rose from 86° C. to 101° C. 90.3 g (0.55 mol) of triethoxysilane was added while maintaining a pot temperature between 86° C.–136° C. The mixture was then maintained at a temperature between 86° C.–106° C. for 4 h and was distilled. 132.4 g (46%) pure of triethoxysilylpropolxyethoxy sulfolane was obtained.

The pure product had a boiling point of 190° C.–194° C. at 4 mm Hg and a density of 1.122 at 25° C. Spectroscopic analysis using proton NMR in $C_6D_6$ yielded resonances at: 0.70(m, 2H), 1.15(t, 9H), 1.75(m, 4H), 2.48(m, 2H), 2.80(m, 4H), 3.13(m, 2H), 3.25(m, 2H), 3.62(m, 1H), and 3.74(q, 6H). Spectroscopic analysis using $^{13}C$ NMR in $C_6D_6$ yielded resonances at: 7.51, 18.91, 24.00, 29.48, 49.82, 57.00, 58.80, 69.03, 70.45, 73.98, and 75.96.

EXAMPLE 6

A 500 ml three neck round bottom flask equipped with a magnetic stirrer, condenser, additional funnel, and pot thermometer was charged with 165.0 g (0.75 mol) of allyloxyethoxy sulfolane under appositive pressure of nitrogen. After heating to 80° C.–90° C., 61.2 g (0.28 mol) of bis(trimethylsiloxy)methylsilane was added, followed by 1 ml of Pt(0)-divinyltetramethyldisiloxane solution in xylene (2 wt % Pt). The pot temperature rose from 86° C. to approximately 102° C. The rest of 122.4 g (0.55 mol) of bis(trimethylsilyl)methylsilane was added while maintaining a pot temperature of between 86° C.–106° C. The mixture was then maintained at a temperature between 86° C.–96° C. for 16 h and was distilled. 167.0 g (50.3%) pure bis(trimethylsiloxy)methylsilylpropoxyethoxy sulfolane was obtained. The pure product had a boiling point of 194° C.–200° C. at 0.4 mm Hg and a density of 1.412 at 25° C.

Spectroscopic analysis using proton NMR in $C_6D_6$ yielded resonances at: 0.11(s, 3H), 0.15(s, 18H), 0.59(m, 2H), 1.69(m, 4H), 2.40(m, 2H), 2.70(m, 2H), 2.78(m, 2H), 3.08(m, 2H), 3.27(m, 2H), and 3.52(m, 1H). Spectroscopic analysis using 13C NMR in $C_6D_6$ yielded resonances at: 0.23, 2.34, 14.44, 24.24, 29.48, 49.75, 56.86, 69.02, 70.51, 74.43, 75.95.

EXAMPLE 7

The bis(trimethylsiloxy)methylsilylpropoxysulfolane of Example 4 was evaluated as a sulfolane functional additive to a silicone elastomer. A room temperature curing 2-part platinum-catalyzed silicone elastomer based on vinyl-terminated polydimethylsiloxane and methylhydrogensiloxane-dimethylsiloxane was cured with the addition of 5 wt % bis(trimethylsiloxy)methylsilylpropoxysulfolane ("additive composition") and without the addition of the sulfolane functional silane("control composition"). The control composition had a contact angle with water of 38°, as compared to a 16° contact angle with water exhibited by the additive composition.

EXAMPLE 8

The experiment of Example 7 was repeated. However, in contrast to the procedure of Example 7, the cure of both the additive composition and the control composition was carried out at 120° C. The control composition had a contact angle with water of 38°, as compared to a 25° contact angle with water exhibited by the additive composition.

EXAMPLE 9

The bis(trimethylsiloxy)methylsilylpropoxysulfolane of Example 4 was evaluated in a surfactant screening application. Bis(trimethylsiloxy)methylsilylpropoxysulfolane was added to deionized water and agitated vigorously for five minutes to prepare a 0.05% solution. Drops of the solution were applied to transparency paper (available from 3M, St. Paul Minn., United States, as 3M™ AF-4300) and compared to deionized water and a solution of 0.5% L-77 polyalkylene oxide modified triloxane (available from by Crompton, Corp, Greenwich, Conn., U.S.A.)

It was observed that the spreading and evaporation of the mixture was intermediate between deionized water and the L-77 solution, indicating that the sulfolane functional silane of the invention exhibited surfactant properties.

EXAMPLE 10

The triethoxysilylpropoxysulfolane of Example 3 was evaluated in an application to stabilize silane hydrosylates. A 1 liter three-neck flask equipped with a magnetic stirrer, pot thermometer and addition funnel was charged with 25 g of 2.5% sodium hydroxide in water. Over a period of approximately twelve minutes, 17 g of triethoxysilylpropoxysulfolane was added followed by 25 g of methacroxypropyltrimethoxysilane. A mild exotherm was observed as the solution became hazy and then cleared. The mixture was stirred until the haze disappeared and the solution was clear. Ethanol and methanol were stripped from the solution at 50° C. at vacuum <15 mm. Water (48 g) was added to the flask to replenish the original volume. Analysis indicated that the stability of silane hydrosylates had been increased by two fold.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A sulfolane functional silane comprising:
   (a) a sulfolane ring;
   (b) an alkoxy group, wherein an oxygen atom of the alkoxy group is bound to the sulfolane ring at a third position of the ring;
   (c) a hydrocarbon backbone having a first terminal carbon atom and a second terminal carbon atom, wherein the backbone has one to fifty carbon atoms and the first terminal carbon is bound to a carbon of the alkoxy group; and
   (d) a silyl moiety comprising at least one hydrolyzable group, wherein the silicon atom of the silyl moiety is bound to the second terminal carbon atom of the hydrocarbon backbone and the at least one hydrolyzable group is represented by the formula $—O—R^2$, wherein $R^2$ is selected from an alkyl group, an alkylamine group, a dialkylamine group, a cyanoalkyl group, an allyl group, a vinyl group, and a cyano group.

2. The sulfolane functional silane of claim 1, wherein the sulfolane ring is substituted.

3. The sulfolane functional silane of claim 1, wherein the alkoxy group has one to four carbon atoms.

4. The sulfolane functional silane of claim 1, wherein the alkoxy group is represented by the formula $—O—(R—O)_n$, wherein R is a linear or branched alkyl group having one to seven carbon atoms, and n is an integer of 1 to 12.

5. The sulfolane functional silane of claim 4, wherein n is an integer of 1 to 4.

6. The sulfolane functional silane of claim 4, wherein R is $—CH_2—CH_2—$.

7. The sulfolane functional silane of claim 1, wherein the hydrocarbon backbone has one to ten carbon atoms.

8. The sulfolane functional silane of claim 1, wherein the hydrocarbon backbone has one to three carbon atoms.

9. The sulfolane functional silane group of claim 1 wherein the silyl moiety comprises two hydrolyzable groups.

10. The sulfolane functional silane of claim 1, wherein the silyl moiety is represented by the formula $—Si(R^3)_m(R^4)_{3-m}$, wherein $R^3$ is independently an alkyl group having one to three carbon atoms and a hydrogen atom, and $R^4$ is independently selected from the group consisting of an alkoxy group having one to three carbon atoms, and m is an integer of 0 to 2.

11. The sulfolane functional silane of claim 1, wherein the silyl moiety comprises at least one siloxane group.

12. The sulfolane functional silane of claim 11, wherein the at least one siloxane group is substituted by $C_1$ to $C_7$ alkyl groups.

13. The sulfolane functional silane of claim 11, wherein the at least one siloxane group is substituted by a group selected from a methyl group, an ethyl group, and a propyl group.

14. The sulfolane functional silane of claim 11, wherein the silyl moiety is represented by the formula $—Si(R^8)_p(R^9)_{3-p}$, wherein $R^8$ is independently an alkyl group having one to three carbon atoms and a hydrogen atom, and $R^9$ is a siloxane group, and p is an integer of 0 to 2.

15. The sulfolane functional silane of claim 14, wherein $R^9$ is a siloxane group substituted with a group selected from a methyl group, an ethyl group and a propyl group.

16. A sulfolane functional silane represented by the formula (VII):

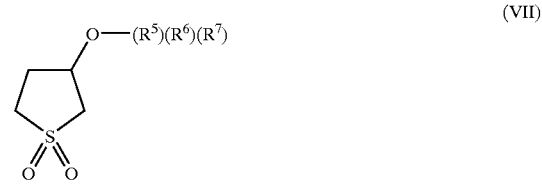

wherein $R^5$ is selected from a substituted or unsubstituted alkyl group having one to ten carbon atoms and the group $(—R—O)_n$, where R is a substituted or unsubstituted, linear or branched alkyl group having one to seven carbon atoms, and n is an integer of 1 to 12;

$R^6$ is a substituted or unsubstituted alkyl group having one to fifty carbon atoms; and $R^7$ is a silyl moiety that comprises a group selected from a siloxane group and a hydrolyzable group represented by the formula $—O—R^2$, wherein $R^2$ is selected from an alkyl group, an alkylamine group, a cyanoalkyl group, an allyl group, a vinyl group, and a cyano group.

17. The sulfolane functional silane group of claim 16, wherein $R^5$ is a substituted or unsubstituted alkoxy group of two to four carbon atoms.

18. The sulfolane functional silane group of claim 16, wherein R 6 is $—CH_2—CH_2—$.

19. The sulfolane functional silane of claim 16, where $R^6$ has one to ten carbon atoms.

20. The sulfolane functional silane of claim 16, wherein $R^6$ has one to three carbon atoms.

21. The sulfolane functional silane of claim 16, wherein $R^7$ is a silyl moiety that comprises one to three siloxane group(s).

22. The sulfolane functional silane of claim 21, wherein the siloxane group(s) are independently substituted by $C_1$ to $C_7$ alkyl groups.

23. The sulfolane functional silane of claim 21, wherein the siloxane group(s) are independently substituted by a group selected from a methyl group, a ethyl group, and a propyl group.

24. A method to stabilize a silane solution, the method comprising adding a sulfolane functional silane represented by the formula (VII):

(VII)

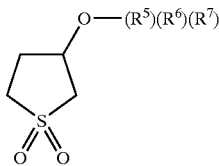

wherein $R^5$ is selected from a substituted or unsubstituted alkyl group having one to ten carbon atoms and the group $(-R-O)_n$, where R is a substituted or unsubstituted, linear or branched alkyl group having one to seven carbon atoms, and n is an integer of 1 to 12;

$R^6$ is a substituted or unsubstituted alkyl group having one to fifty carbon atoms; and $R^7$ is a silyl moiety that comprises at least one hydrolyzable group, to a solution containing silane hydrosylates.

25. A surfactant comprising the sulfolane functional silane represented by the formula (VII):

(VII)

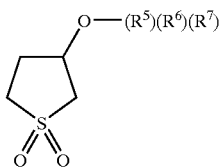

wherein $R^5$ is selected from a substituted or unsubstituted alkyl group having one to ten carbon atoms and the group $(-R-O)_n$, where R is a substituted or unsubstituted, linear or branched alkyl group having one to seven carbon atoms, and n is an integer of 1 to 12;

$R^6$ is a substituted or unsubstituted alkyl group having one to fifty carbon atoms; and $R^7$ is a silyl moiety that comprises at least one siloxane group.

26. The surfactant of claim 25, wherein the at least one siloxane group(s) is independently substituted by $C_1$ to $C_7$ alkyl groups.

27. The surfactant of claim 25, wherein the at least one siloxane group(s) is independently substituted by a group selected from a methyl group, an ethyl group, and a propyl group.

28. An elastomeric composition comprising an elastomeric polymer and a sulfolane functional silane represented by the formula (VII):

(VII)

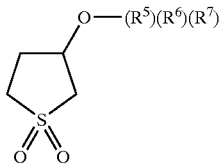

wherein $R^5$ is selected from a substituted or unsubstituted alkyl group having one to ten carbon atoms and the group $(-R-O)_n$, where R is a substituted or unsubstituted, linear or branched alkyl group having one to seven carbon atoms, and n is an integer of 1 to 12;

$R^6$ is a substituted or unsubstituted alkyl group having one to fifty carbon atoms; and $R^7$ is a silyl moiety that comprises at least one non-hydrolyzable group that is a substituted or unsubstituted siloxane group.

29. A method of enhancing the wettability of an elastomer, the method comprising compounding an uncured elastomeric polymer with an additive, wherein the additive comprises a sulfolane functional silane represented by the formula (VII):

(VII)

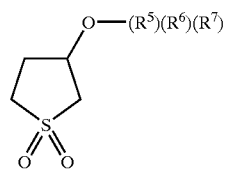

wherein $R^5$ is selected from a substituted or unsubstituted alkyl group having one to ten carbon atoms and the group $(-R-O)_n$, where R is a substituted or unsubstituted, linear or branched alkyl group having one to seven carbon atoms, and n is an integer of 1 to 12;

$R^6$ is a substituted or unsubstituted alkyl group having one to fifty carbon atoms; and $R^7$ is a silyl moiety that comprises at least one non-hydrolyzable group that is a substituted or unsubstituted siloxane group.

30. An additive for use in enhancing the wettability of an elastomeric composition, the additive comprising a sulfolane functional silane represented by the formula (VII):

(VII)

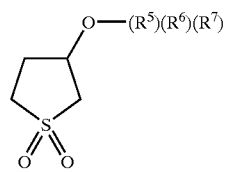

wherein $R^5$ is selected from a substituted or unsubstituted alkyl group having one to ten carbon atoms and the group $(-R-O)_n$, where R is a substituted or unsubstituted, linear or branched alkyl group having one to seven carbon atoms, and n is an integer of 1 to 12;

$R^6$ is a substituted or unsubstituted alkyl group having one to fifty carbon atoms; and $R^7$ is a silyl moiety that comprises at least one non-hydrolyzable group that is a substituted or unsubstituted siloxane group.

31. A sulfolane functional silane comprising:
(a) a sulfolane ring;
(b) an alkoxy group that is represented by the formula $-O-(R-O)_n$, wherein R is a linear or branched alkyl group having one to seven carbon atoms, and n is an integer of 1 to 12, and an oxygen atom of the alkoxy group is bound to the sulfolane ring;
(c) a hydrocarbon backbone having a first terminal carbon atom and a second terminal carbon atom, wherein the backbone has one to fifty carbon atoms and the first terminal carbon is bound to a carbon of the alkoxy group; and (d) a silyl moiety, wherein the silicon atom of the silyl moiety is bound to the second terminal carbon atom of the hydrocarbon backbone.

32. The sulfolane functional silane of claim 31, wherein n is an integer of 1 to 4.

33. The sulfolane functional silane of claim 31, wherein R is —$CH_2$—$CH_2$—.

34. The sulfolane functional silane of claim 31, wherein the hydrocarbon backbone has one to ten carbon atoms.

35. The sulfolane functional silane of claim 31, wherein the hydrocarbon backbone has one to three carbon atoms.

36. The sulfolane functional silane of claim 31, wherein the silyl moiety comprises one hydrolyzable group.

37. The sulfolane functional silane of claim 36, wherein the silyl moiety comprises two hydrolyzable groups.

38. The sulfolane functional silane of claim 36, wherein the at least one hydrolyzable group is represented by the formula —O—$R^2$, wherein $R^2$ is selected from an alkyl group, an alkylamine group, a dialkylamine group, a cyanoalkyl group, an allyl group, a vinyl group, and a cyano group.

39. The sulfolane functional silane of claim 16, wherein $R^7$ comprises two hydrolyzable groups.

* * * * *